United States Patent

Miller

[11] 4,053,520
[45] Oct. 11, 1977

[54] PRODUCTION OF PARA-DIALKYLBENZENE DIHYDROPEROXIDE

[75] Inventor: Glenn E. Miller, Pasadena, Tex.

[73] Assignee: The Goodyear Tire & Rubber Company, Akron, Ohio

[21] Appl. No.: 544,922

[22] Filed: Jan. 28, 1975

Related U.S. Application Data

[62] Division of Ser. No. 34,455, May 5, 1970, Pat. No. 3,883,600.

[51] Int. Cl.² .......................................... C07C 179/02
[52] U.S. Cl. ............................ 260/610 A; 260/610 B
[58] Field of Search ..................... 260/610 B, 610 A

[56] References Cited

U.S. PATENT DOCUMENTS

| | | | |
|---|---|---|---|
| 2,915,557 | 12/1959 | Kreps et al. | 260/610 A |
| 2,915,558 | 12/1959 | Alder et al. | 260/610 A |
| 3,883,600 | 5/1975 | Miller | 260/610 B |

Primary Examiner—James O. Thomas, Jr.
Assistant Examiner—W. B. Lone
Attorney, Agent, or Firm—Browning, Bushman & Zamecki

[57] ABSTRACT

A continuous process for producing para-dialkylbenzene dihydroperoxide by the liquid phase oxidation of para-dialkylbenzene with molecular oxygen in the presence of an aqueous alkali metal hydroxide wherein the para-dialkylbenzene dihydroperoxide is recovered substantially free of water, monohydroperoxide and unreacted dialkylbenzene and wherein the monohydroperoxide and unreacted dialkylbenzene are treated to produce a material low in impurities suitable for recycle to the oxidation reactor.

1 Claim, 1 Drawing Figure

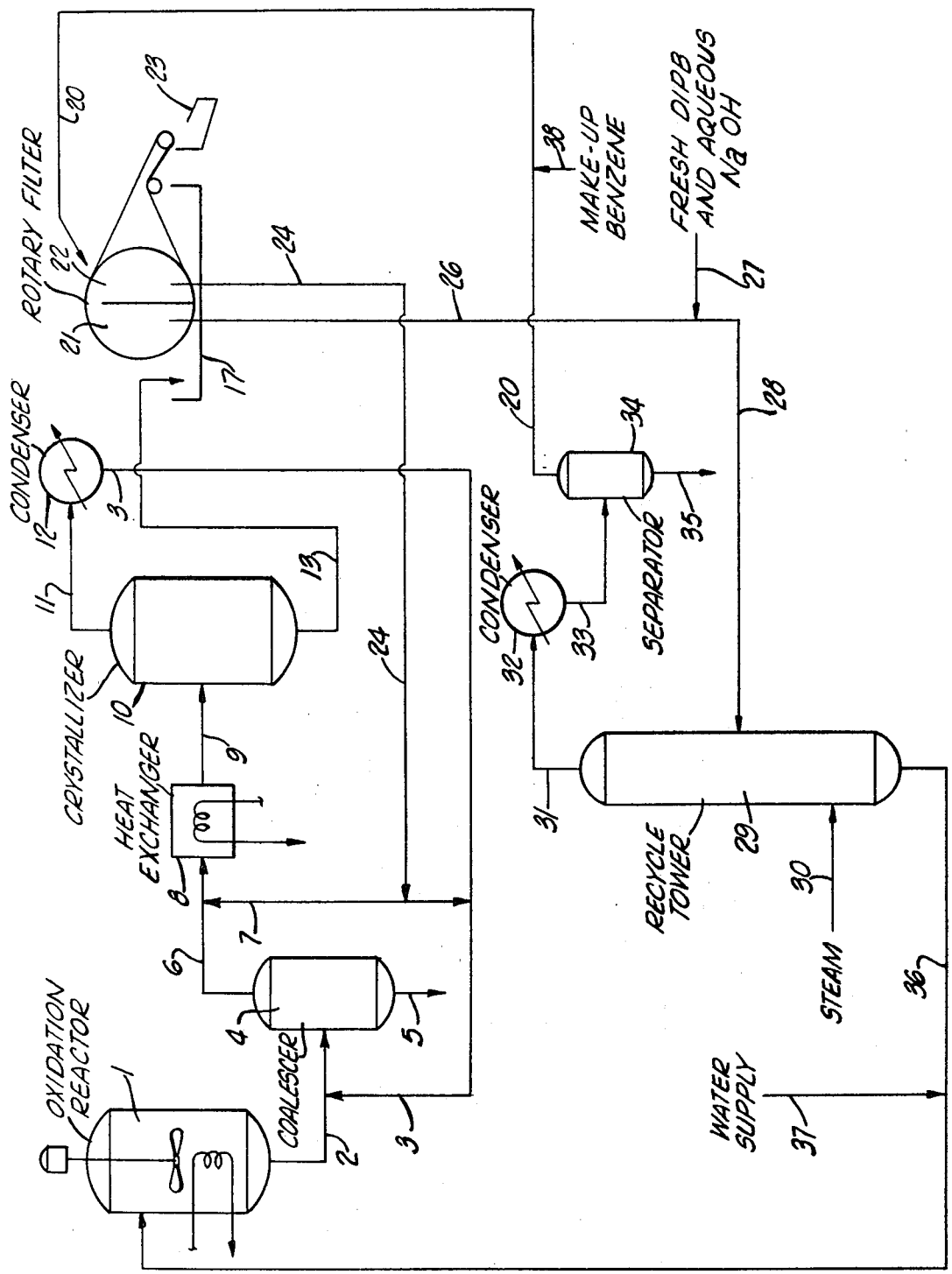

PRODUCTION OF PARA-DIALKYLBENZENE DIHYDROPEROXIDE

This is a division of application Serial No. 34,455 filed May 5, 1970, now U.S. Pat. No. 3,883,600.

FIELD OF THE INVENTION

The process of this application relates to the following steps (all of which are well known in the prior art): oxidizing para-dialkylaromatic hydrocarbons with molecular oxygen under suitable temperature and pressure conditions to yield an oxidation reaction product containing para-dialkylaromatic dihydroperoxides treating the oxidation reaction product to recover the dihydroperoxides, and recycling the remainder of the oxidation reaction product, containing unoxidized dialkylaromatic hydrocarbon and paritally oxidized dialkylaromatic hydrocarbon to the oxidation reactor.

BACKGROUND OF THE INVENTION

The oxidation reaction commonly used for preparing dihydroperoxides such as para-diisopropylbenzene dihydroperoxide includes oxidation of the para-dialkylaromatic with molecular oxygen in the presence of an aqueous alkaline material at increased pressure and temperature. In preparing the dihydroperoxides by such an oxidation reaction, it is the practice to continue the reaction only partially to completion (based upon the total dialkylbenzene present) since as the oxidation reaction is carried further toward completion, an even increasing amount of the dialkylbenzene is connected to undesireable oxidation products, such as carboxylic acids and ketones. Thus, since the oxidation reaction is carried only to partial completion, large amount of monohydroperoxide, the dihydroperoxide intermediate, as well as unreacted dialkylbenzene are present in the oxidation reaction mixture.

The oxidation reaction to produce dihydroperoxides from para-dialkylaromatic hydrocarbons is inhibited by certain materials such as phenolics which may occur in the dialkylbenzene feed to the oxidation reaction. Also, acidic materials such as carboxylic acids may cause rearrangement of the hydroperoxides formed in the oxidation reaction, to phenolics, thereby inhibiting the oxidation reaction. It is known to treat the dialkylbenzene feed to the oxidation reaction with strong aqueous solutions of alkali metal hydroxides whereby the unwanted inhibitor compounds will react to form water soluble salts of the phenolics and carboxylic acids, which may be then separated from the dialkylbenzene. Such a treatment process requires a special dialkylbenzene treatment facility and requires an excess amount of alkali metal hydroxide to ensure the complete removal of such inhibitors. The para-dialkylaromatic dihydroperoxides are conveniently recovered from the oxidation reaction mixture by a crystallization technique. However, significant amounts of the mono-hydroperoxide and unreacted dialkylbenzene are retained in the solid dihydroperoxide product. It is desirable to separate the monohydroperoxide and the dialkylbenzene from the dihydroperoxide to achieve improved quality of the latter product as well as to recover the valuable precursors for recycle to the oxidation reaction. In a continuous reaction to produce dihydroperoxide from dialkylbenzenes employing a recycle stream comprising monohydroperoxide and unreacted dialkylbenzene, care must be taken to prevent the increase in concentration of unwanted reaction by-products, particularly carboxylic acids. These by-products, unless removed from the reation system, will increase in concentration until they begin to interfere with the oxidation reaction. Where an aqueous alkaline material is employed within the oxidation reaction, substantial amount of by-products such as carboxylic acids and phenolic materials will react to form their sodium salts which are soluble in the aqueous phase. Good separation of the aqueous phase from the organic reaction product will ensure that these by-prodoucts will be removed as they are formed. Other oxidation by-products, comprising such compounds as alpha, alpha' -dihydroxy dialkyl benzene and alpha hydroxy - alpha' hydroperoxy dialkylbenzene tend to crystalize along with the dihydroperoxides whereby they are conveniently removed from the oxidation system. These by-products, if allowed to increase in the oxidation reaction system, will adversely affect the oxidation by their dilution effect. Additionally, they are further oxidized to such unwanted by-products as carboxylic acids and acetophenone-type compounds. These by-products, as they crystallize with the dihydroperoxides, are conveniently removed from the oxidation system with the dihydroperoxides. The dihydroperoxides containing these by-products may be utilized, for instance in the production of dihydric phenols by acid catalyzed rearrangement, or the dihydroperoxides may be further purified to remove such by-products.

The oxidation reaction products remaining after the para-dialkylaromatic dihydroperoxide is recovered comprise unreacted para-dialkylaromatic hydrocarbon and para-dialkylaromatic monohydroperoxide, both of which are precursors of the para-dialkylaromatic dihydroperoxide. The prior art teaches that these materials may be recycled to the oxidation reaction for conversion into additional amounts of para-dialkylbenzene dihydroperoxide.

SUMMARY OF THE INVENTION

The present invention is directed to a continuous process for producing aromatic dihydroperoxides such as para-diisopropylbenzene dihydroperoxide or para-di(sec-butyl) benzene dihydroperoxide, wherein the mono-hydroperoxides and unreacted dialkylbenzenes are recovered in a form suitable for conversion into additional amounts of the dihydroperoxides.

The aromatic dihydroperoxides have found use as oxidizing agents and free radical initiators for a number of polymerization processes are valuable in preparing dihydric phenols such as hydroquinone and resorcinol. In preparing the dihydric phenols, it is well known to rearrange the dihydroperoxide in the presence of an acid catalyst to form the corresponding phenol and carbonyl compound.

The continuous process of this invention encompasses three important process aspects. The first is directed to the treatment of the product of an oxidation reaction wherein a dialkylaromatic hydrocarbon is oxidized with molecular oxygen in the presence of an aqueous alkali metal hydroxide at conditions of elevated temperature and pressure. The oxidation reaction product which contains significant amount of water, dihydroperoxide, mono-hydroperoxide, dialkylbenzene and reaction side products is intermixed with a first hydrocarbon stream comprising a major amount of a hydrocarbon that forms a minimum boiling azeotrope with water and in which the dihydroperoxide is relatively insoluble and the monohydroperoxide soluble at temperatures below about 100° F. The aqueous phase is then separated from the organic phase to remove water and water soluble impurities. The dewatered organic phase is contacted with a second hydrocarbon stream comprising the same major component as the first hydrocarbon stream, and any residual water removed from the organic phase by vaporizing the hydrocarbon-water azeotrope, thereby producing an organic phase substantially free of water and water soluble impurities. The hydrocarbon-water azeotrope vapor is condensed and the condensed hydrocarbon returned to the first hydrocarbon stream.

The second aspect of my process involves further treatment to recover a solid dihydroperoxide product and a liquid filtrate stream comprising monohydroperoxide and unreacted dialkylbenzene. This is accomplished by cooling the organic phase to a temperature blow about 100° F. to crystallize substantially all of the dihydroperoxide from the organic phase, and separating the crystallized dihydroperoxide, wet with liquid organic material, from a liquid filtrate which is treated for recycle to the oxidation reactor. The wet crystalized dihydroperoxide is washed with a third hydrocarbon stream comprising a major amount of the same hydrocarbon as the first and second hydrocarbon streams, and the solid product dihydroperoxide substantially free of mono-hydroperoxide and dialkylbenzene is separated from the third hydrocarbon wash material. The wash liquid stream is recycled to the first and second hydrocarbon streams. The liquid filtrate recovered in the first solid separation, contains mono-hydroperoxide and dialkylbenzene which are precursors to the dihydroperoxide, and must be recycled to the oxidation reaction in an efficient process for dihydroperoxide production. Before recycling to the oxidation reaction, however, further treatment to remove the hydrocarbon is preferred. In operating a continuous process it is necessary to provide dialkylbenzene to replace that consumed in the oxidation reaction. The oxidation reaction is promoted by removing from the fresh dialkylbenzene certain impurities which retard the oxidaton reaction.

The third aspect of my process is directed to a method of treating the liquid filtrate from the first solids separation with the fresh dialkylbenzene to produce a superior quality feed material for the oxidation reactor free of materials which will retard or inhibit the oxidation reaction. This is accomplished by combining the liquid filtrate with a mixture of fresh dialkylbenzene and aqueous sodium hydroxide, and treating this new mixture in a stream stripping column to recover an overhead product and a bottoms liquid product wherein, the overhead vapor product comprises stripping steam and hydrocarbon substantially free of dialkylbenzene, the bottoms, a liquid product, comprising mono-hydroperoxide, dialkylbenzene and aqueous sodium hydroxide are diluted with condensed stripping steam, free of oxidation inhibiting impurities. This bottoms product is recycled to the oxidation reactor as feed meterial, and the overhead product is dewatered and recycled to the third hydrocarbon stream. This continuous process provides an efficient method for producing dihydroperoxide in good yield wherein the mono-hydroperoxide and unreacted dialkylbenzene are recovered and recycled to the oxidation reactor. Additional advantages include efficient water removal from the dihydroperoxide product, good recovery of mono-hydroperoxide and unreacted dialkylbenzene for recycle to the oxidation reactor, effective removal of undesirable materials which inhibit the oxidation reaction, and effective prevention of an unwanted build-up of oxidation reaction side products. These as well as other advantages will be more specifically pointed out in the following description of the invention.

BRIEF DESCRIPTION OF THE DRAWING

The accompanying drawing is a schematic representation of the processing steps and flows employed in carrying out the method of the invention in a continuous manner.

DETAILED DESCRIPTION OF THE INVENTION

The oxidation of dialkylaromatic hydrocarbons such as para-diisopropylbenzene and para-di(sec-butyl) benzene with molecular oxygen to produce dialkylbenzene dihydroperoxides in conveniently carried out in the presence of an aqueous alkaline material such as sodium hydroxide. The sodium hydroxide serves to react with acidic materials present which tend to inhibit the reaction. In the oxidation process conducted according to the present invention, the reaction mixture comprises an aqueous phase and an organic phase. The range of sodium hydroxide concentration in the aqueous phase may be from about 0.5% to about 10%, preferably from about 0.8 to about 1.2%. The aqueous phase may comprise from about 5% to about 50% of the total reaction mixture. Since water is essentially just a diluent, the amount of water present is not critical, however the preferred amount of aqueous is from abut 5 to 15%.

The preferred practice is to continue the oxidation reaction only partially to completion, that is, until the hydroperoxide concentration of the organic phase is between about 30% and about 55% preferably about 40 to 50%, calculated as dihydroperoxide. At this conversion level, substantial amounts of dialkylaromatic mono-hydroperoxide and unreacted dialkylbenzene hydrocarbon are present in the oxidation reaction product. At these hydroperoxide concentrations the oxidation product becomes very viscous, and the specific gravity of the organic phase approaches the specific gravity of water, thereby making water separation and product recovery difficult. I have found that by treating the oxidation reaction product with a water in soluble hydrocarbon, which is miscible with the organic phase of the reaction product, that the separation of the aqueous phase from the organic oxidate is greatly facilitated. The selected hydrocarbon useful in my invention may be any hydrocarbon which forms a low boiling azeotrope with water and will not oxidize at the operating conditions in the oxidation. The dihydroperoxide formed must be relatively insoluble in the hydrocarbon. Benzene, tolulene, and xylene are examples of hydrocarbons which meet all the necessary criteria mentioned above. It is preferred to treat the oxidation reaction product with hydrocarbon in a volume ratio of hydrocarbon to organic phase of between about 0.05:1 to about 0.2:1 and at a temperature between about 160° F and about 230° F. The hydrocarbon serves to decrease the specific gravity and the viscosity of the organic phase, thereby facilitating the separation of the organic and aqueous phases. Treatment of the oxidation reaction product in an amount less than the minimum ratio is insufficient to cause good separation of the phases, and hydrocarbon present in an amount greater than the maximum ratio does not contribute any substantial additional separation ability to the oxidation reaction product. It is necessary to maintain the temperature of this mixture above about 160° F to prevent crystallization of dihydroperoxide from the organic solution. The crystallization of dihydroperoxide before the water is separated from the oxidation reaction product interferes with such water separation. The hydroperoxides produced by this oxidation reaction are heat sensitive and will decompose if too much heat is applied and the temperature should be maintained below 300° F. The maximum temperature of 230° F has been chosen as being well below the temperature at which spontaneous decomposition might occur. Pressure is conveniently be maintained to keep the mixture in the liquid phase.

The aqueous phase may be separated from the organic phase by any convenient method, such as gravity settling and subsequent decantation, centrifugation, or passing the hydrocarbon treated oxidation reaction product through a coalescer element. Separation of the aqueous phases aids in the subsequent processing of the organic phase and the water, which has deleterious effect on the subsequent reaction of the dihydroperoxides, is removed. The water soluble sodium salts of reaction by-products, e.g. phenolics and carboxylic acids are also removed in the aqueous phase. These salts, if allowed to accumulate in the reaction system, will inhibit the oxidation reaction. The salts would also interfere with the subsequent uses of the dihydroperoxide. Any excess sodium hydroxide, which will interfere with the acid catalyzed rearrangement of the dihydroperoxide, is also removed in the aqueous phase. The hydrocarbon stream used to treat the oxidation reaction product need not be of ultra high purity. It is convenient to utilize recycle hydrocarbon streams from the dihydroperoxide recovery process.

After separation of the aqueous phase, the organic phase is treated with a second hydrocarbon stream at a temperature in a volume ratio of hydrocarbon to organic phase from about 0.2 to 1 to about 0.5 to 1. The preferred temperature for such treatment is between about 160° F and about 230° F. Below about 160° F the dihydroperoxide tends to precipitate upon the addition of the hydrocarbons, this causing materials handling problems. Above 230° F the hydroperoxides become subject to thermal degradation. The hydrocarbon used for this treatment may be fresh or may be a recycle stream from the dihydroperoxide recovery process. The hydrocarbon used as the second hydrocarbon stream is the same hydrocarbon used for the first hydrocarbon stream. A hydrocarbon recycle stream particularly useful for this treatment is that recovered from the dihydroperoxide cake wash, as is subsequently described. This treatment of the organic phase with the hydrocarbon and the subsequent cooling of the organic phase to a temperature below about 100° F causes the dihydroperoxide to crystallize in a manner such that only very small amounts of dialkylbenzene and dialkylbenzene mono-hydorperoxide are occluded or adsorbed upon the dihydroperoxide crystals.

The separation of the aqueous phase from the organic phase may not be complete, and small amounts of water may remain in the organic phase. After the second hydrocarbon addition, any residual water may be removed by vaporizing the water as the hydrocarbon-water azeotrope. This vaporization may be performed at atmospheric pressure or at reduced pressure. The azeotrope of benzene and water, for example, boils at 156° F at atmospheric pressure and boils at lower temperatures as the pressure is reduced. Such vaporization ensures that all the water is removed from the organic phase and aids in improving the quality of the dihydroperoxide products since water is an undesirable impurity in the dihydroperoxide product which is to be rearranged to produce a dihydric phenol. The vaporization of the water azeotrope can be accomplished by heating the organic phase with heating means such as steam coils, heating jackets, or any convenient heating means. The hydrocarbon-water azeotrope can be vaporized under vacuum conditions, in which case the azeotrope boiling point will be reduced to a lower temperature, depending upon the value of the vacuum applied. by vaporizing the azeotrope under vacuum conditions, the temperature of the oxidate can be reduced substantially. For example, at an absolute pressure of 54 Hq the benzene-water azeotrope boils at 84° F, compared to a boiling point of 156° F at 760 maximum Hq. This temperature reduction will cause the para-dialkylbenzene dihydroperoxide to separate from the organic phase as solid cyrstals. Thus, in one embodiment of this invention, the organic phase, after the first water separation, is treated with the second hydrocarbon stream and then is subjected to vacuum conditions to cause the hydrocarbon-water azeotrope to vaporize and at the same time the temperature reduction will cause the paradialkylaromatic dihydroperoxide to crystallize from the liquid organic phase. Should it be undesirable to employ vacuum conditions, then the hydrocarbon-water azeotrope may be removed at about atmospheric pressure by heating the oxidate to the azeotrope boiling point. The para-dialkylbenzene dihydroperoxide is then recovered by cooling the organic phase to a temperature below about 100° F by a convenient cooling means such as a heat exchanger.

Upon condensing, the hydrocarbon-water azeotrope will separate into a hydrocarbon layer and a water layer. The water is conveniently discarded along with the aqueous phase previously removed from the organic phase. The hydrocarbon is, for economic reasons, recycled within the dihydroperoxide separation process, rather than discarding and using fresh make-up hydrocarbon.

Upon crystallization of the dihydroperoxide from the organic phase, the slurry formed is subjected to a first solid-liquid separation to yield a solid dihydroperoxide and a liquid filtrate. The solid dihydroperoxide may be separated by any convenient means, such as settling and decantation, filtration, centrifugation or other solid-liquid separation means. It is advantageous to remove as much liquid filtrate as possible from the solid dihydroperoxide to improve the product purity. The solid dihydroperoxide is recovered from the first solid-liquid separation and is then treated further to improve its purity. The liquid filtrate is treated further to produce a material suitable for recycle to the oxidation reaction.

The solid dihydroperoxide, recovered from the first solid-liquid separation is treated with a suitable hydrocarbon wash in a volume ratio of hydrocarbon to solid of about 1/1 to about 3/1 weight ratio and the solid dihydroperoxide is subjected to a second solid-liquid separation to remove the wash liquid. The wash liquid or third hydrocarbon stream, is of the same hydrocarbon used for the first and second hydrocarbon stream. The wash liquid recovered from the second solid liquid separation is substantially hydrocarbon with a small concentration of liquid oxidate. This wash is recycled to the first or second hydrocarbon streams, preferably into the second hydrocarbon stream used to treat the oxidate prior to dihydroperoxide crystallization. The solid dihydroperoxide, substantially free of monohydroperoxide and dialkylaromatic hydrocarbons, is recovered from the solids-liquid separation step as the product dihydroperoxide. The wash liquid recovered is substantially all hydrocarbon with a small concentration of liquid organic phase. By recycling the wash liquid to the second hydrocarbon stream, all the liquid organic phase components are returned to the process and an economical usage of hydrocarbon is achieved.

The liquid filtrate recovered from the first solid-liquid separation is treated to produce a material suitable for feed to the oxidation reaction. The liquid filtrate is combined with a mixture comprising fresh dialkylaromatic and an aqueous solution of sodium hydroxide. The dialkylaromatic is provided as make-up for the dialkylaromatic consumed in the oxidation reaction, and is supplied in such an amount that the oxidation reaction can be continuously operated. The aqueous solution of sodium hydroxide fed to the steam stripping column must be of such concentration that, after dilution in the steam stripping column, the aqueous phase of the steam stripping column bottoms will contain from about 0.5 wt.% to about 10 wt.% sodium hydroxide. The concentration of aqueous sodium hydroxide fed to the steam stripping column will depend on several operational factors and must be worked out for each individual case. The operational factors which control the required aqueous sodium hydroxide concentration include: quality of the stripping steam; heat loss from the steam stripping column; reflux ration employed in the steam stripping column; and the amount of impurities in the steam stripping column feed which will consume sodium hydroxide. The various impurities present in the fresh dialkylaromatic and the liquid filtrate, such as phenols and carboxylic acids, will inhibit the oxidation reaction. The sodium hydroxide added with the steam stripping column feed, reacts with such impurities, thus rendering them innocuous to the oxidation reaction.

The sodium hydroxide added to the steam stripping column in excess of the amount required to react with the impurities present, is employed in the oxidation reactor to consume acidic by-products of the oxidation reaction. The sodium hydroxide added to the steam stripping column should be from about 0.05 wt.% to about 0.15 wt.% of the total steam stripping bottoms; and as described above, must be present in an aqueous solution of from about 0.5 wt.% to about 1.5 wt.% concentration.

The mixture of liquid filtrate, fresh dialkylaromatic, and aqueous sodium hydroxide fed to the steam stripping column contains a substantial amount of hydrocarbon in solution. This hydrocarbon is removed in the steam stripping column and the remaining mixture is supplied as feed to the oxidation reactor. This hydrocarbon, upon recovery, is recycled for use in the dihydroperoxide recovery process, such as in the first and second hydrocarbon streams used to treat the oxidate and in the wash liquid for the solid dihydroperoxide. To remove the hydrocarbon, the liquid filtrate, fresh dialkylbenzene and aqueous sodium hydroxide mixture is treated in a stream stripping column wherein the hydrocarbon is removed overhead as a vapor substantially free of dialkylbenzene. As the hydroperoxide components of the liquid filtrate are heat sensitive and will decompose to a great extent at about 300° F, it is desirable to perform the steam stripping operation at a temperature below such temperature. In order to maintain the desired operating temperature, the steam stripping column is operated at atmospheric pressure and a steam to hydrocarbon weight ratio of about 0.10/1 to about 1/1, to maintain the steam stripping column operating temperature between about 212° and 230° F. The steam which supplied the sensible heat to the steam stripper and the steam required to supply the heat of vaporization for the hydrocarbon, will condense. This condensed steam serves to dilute the aqueous sodium hydroxide fed into the steam stripping column until the sodium hydroxide is present in aqueous solution at about 0.5 wt.% to about 1.5 wt.%. The aqueous sodium hydroxide solution in the steam stripping column serves to stablize the hydroperoxide present, and thereby prevents decomposition of the dialkylbenzene hydroperoxide. It also functions to deactivate oxidation inhibitors such as phenolics and carboxylic acids. From the bottom of the steam stripping column, a mixture free of hydrocarbon comprising liquid filtrate, fresh dialkylbenzene and dilute sodium hydroxide is recovered to be used as feed to the oxidation reactor. This mixture is substantially free of the hydrocarbon, although small amounts of hydrocarbon will not affect the oxidation reaction as the hydrocarbon selected are stable under the oxidizing conditions employed to produce the desired dihydroperoxides. Substantial amount of hydrocarbon in the oxidation reactor feed effect the reaction by taking up reactor volume which otherwise is utilized for producing dihydroperoxides. Therefore, the best practice is to remove substantially all the hydrocarbon from the steam stripping column bottoms mixture. This mixture contains unreacted dialkylbenzene which is oxidized to hydroperoxides in the oxidation reactor, and dialkylbenzene monohydroperoxide which is oxidized further to produce dihydroperoxides.

The sodium hydroxide, in the oxidation reaction, serves to react with acidic reaction by-products and also with phenolic materials which would otherwise inhibit the hydroperoxidation reaction. The sodium salts of these by-products are water soluble and are therefore removed from the oxidation reaction system with the oxidation reaction product aqueous phase.

The following example is provided to specifically illustrate the method by which the invention is carried out and the advantages obtained therefrom.

DETAILED DESCRIPTION OF THE DRAWING

Referring to the drawing, the oxidation of the dialkyl aromatic is performed in the oxidation reactor 1. The flow diagram will be described by reference to the oxidation of diisopropylbenzene to its dihydroperoxide using benzene as the hydrocarbon solvent. The oxidation reaction product which comprises an aqueous phase and an organic phase, is continuously transferred from the oxidation reactor 1 through line 2 to a phase separation, e.g. coalescer 4, wherein the aqueous phase is separated from the organic phase and discarded through line 5. An internally recovered benzene stream is recycled through line 3 into the oxidation reaction product stream discharge line 2. This benzene recycle added to the oxidation products provides a solvent for impurities and provides means for removing the aqueous phase. The addition of the benzene recycle stream to the product line 2 also provides a greater gravity difference between the aqueous and organic phases which lends to better phase separation in the coalescer 4.

The organic phase is withdrawn from the coalescer 4 through line 6 and is mixed with a second internally produced benzene stream which is injected through line 7. If a phase separator is used which can tolerate solids, then the cake wash liquid or weak filtrate from line 24 may be fed to the oxidation reaction product ahead of the phase separator 4, i.e. the weak filtrate in line 24 may be fed directly to line 2. Benzene additions to the crystallizer feed in addition to azeotroping water and removing impurities, provides means for optimizing the vacuum-temperature relationship in the crystallizer and also allows better crystallization by reducing the viscosity. The optimization of the vacuum-temperature relationship of the crystallizer feed is facilitated by addition of the recycle streams containing benzene which avoids the necessity to operate at lower vacuums in the crystallizer 10.

The temperature of the organic phase from the coalescer may be adjusted to optimize the vacuum-temperature relationship before it is fed to crystallizer 10 through line 9, by heating or cooling the product in heat exchanger 8.

Any water remaining in the organic phase in the crystallizer is removed overhead through line 11 as a benzene-water azeotrope vapor and is condensed in condenser 12 and recycled to the oxidation reaction product through line 3 as mentioned above. In the crystallizer 10, a temperature drop is effected by vacuum distillation of the benzene, and the benzene-water azeotrope is removed overhead through line 11. The slurry from the crystallizer which still contains some benzene, is fed to a rotary drum filter 17.

The rotary drum filter which is of a conventional design, has two filter sections 21 and 22. A strong liquid filtrate is removed from the first section 21 through line 26 and prepared for recycle to the oxidation reactor 1 as will be described below. The filter cake from rotary drum filter section 21 is transferred to the second section 22 on a filter cloth and is washed with a benzene stream fed to the filter section through the line 20. The wash liquid or weak filtrate is withdrawn from the second section of the filter through line 24 and recycled to the crystallizer feed as mentioned previously. A solid dihydroperoxide product substantially free of mono-hydroperoxide and dialkylbenzene is discharged from the filter apparatus to a suitable conveyor or receptacle 23.

The filtrate recovered from the first section of the rotary drum filter is mixed in line 26 with fresh feed dialkylbenzene and an aqueous sodium hydroxide solution, which are fed to the strong filtrate through line 27. This mixture is then fed through line 28 to a steam stripping or recycle column 29, wherein benzene is stripped from the filtrate mixture and the filtrate to which the fresh feed has been added, is prepared for recycle to the oxidation reactor 1. Stripping steam is fed to the stripping column 29 via line 30. Steam and vaporized benzene are removed from the steam stripping column 29 overhead through line 31 and condensed in a conventional condenser 32. The condensate, comprising a mixture of benzene and water, is fed through line 33 to a separator 34 wherein water is separated from the benzene and discarded from the system through line 35. Benzene is withdrawn overhead from the separator 34 in relatively high purity, through line 20 and utilized as the filter cake wash which is fed to the second section of the rotary drum filter 22 through line 20. Make up benzene may be added to the system by adding to the recycle line 20 through line 38.

The liquid bottoms material from the steam stripping column, comprises diisopropyl benzene, mono-dihydroperoxide and aqueous sodium hydroxide, which is diluted with the condensed stripping steam added to the column 29 to vaporize benzene. This liquid bottoms material from the stripping column 29, is treated with water through line 37 to adjust the sodium hydroxide in the aqueous phase to a concentration of about 1 wt.% and the bottoms material is then recycled through line 36 to the oxidation reactor 1.

EXAMPLE

The process of my present invention is practiced in an apparatus arranged according to the flow diagram shown in the drawing. The oxidation reaction product obtained from the reactor 1 comprised about 12% dihydroperoxide, 32% monohydroperoxide, 13% dialkylbenzene, and 11% aqueous phase and the remainder oxidation reaction side products. The oxidation reactor is operated at about 230° F at a pressure of about 255 to 300 psig and for a residence time of about one hour. Benzene is added through line 3 to the oxidation reaction product in line 2 in a ratio of benzene to oxidation reaction product of about 0.12 to 1. The organic phase removed from the coalescer through line 6 is contacted with a second benzene stream through line 7 in a ratio of benzene to organic phase of about 0.3 to 1. The crystallizer 10 is run at a temperature of about 85° F at a pressure of about 50 millimeters mercury absolute. The azeotropic mixture condensed in condenser 12 comprises about 90% benzene and 10% water. The liquid in the crystallizer 10 drops to a temperature of about 90° F. The slurry discharge from the crystallizer 10 through line 13, contains about 25% benzene as liquid. The filter cake was washed in the second section of the rotary filter drum with benzene in a weight ratio of benzene to solid dihydroperoxide of about 2 to 1.

The temperature of the steam stripping column is maintained below about 230° F since the hydroperoxides in the recycle stream are heat sensitive. To maintain the desired temperature and to strip substantially all the benzene from the liquid phase, it is necessary to supply about 0.65 pounds of steam per pound of benzene to be removed.

The product dihydroperoxide obtained is substantially free of dialkylbenzene and monohydroperoxide and the efficiency of the reaction was calculated to be about 70% of the dialkylbenzene charged to the reactor is recovered as dihydroperoxide. The remaining 30% of the dialkylbenzene feed is converted to side products which are removed from the system as water soluble salts via line 5 and as impurities in the dihydroperoxide cake recovered at 23.

while my invention has been described and illustrated herein with a certain degree of particularity by reference to a specific embodiment, it is to be understood that my invention is not limited to the exemplary system set forth, but rather should be afforded the full scope of the appended claims.

I claim:

1. A process for the recovery of a paradialkylbenzene dihydroperoxide selected from the group consisting of para-diisopropylbenzene dihydroperoxide and para-di (sec-butyl) benzene dihydroperoxide from an oxidation reaction product comprising water, dihydroperoxide, monohydroperoxide, dialkylbenzene and other oxidation reaction products, which comprises the following steps:

a. treating the oxidation reaction product to separate an aqueous phase and an organic phase, b. treating the organic phase with a hydrocarbon stream comprising a hydrocarbon in which the dihydroperoxide is insoluble and the monohydroperoxide and dialkylbenzenes are soluble below about 85° F, which forms a minimum working azeotrope with water and which is selected from the class consisting of benzene, toluene and xylene, in a minimum ratio of hydrocarbon to organic phase of about 0.05:1, c. cooling the organic phase-hydrocarbon mixture to a temperature below about 85° F for a time sufficient to allow the dihydroperoxide to crystallize from said organic phase-hydrocarbon mixture, d. separating the crude solid dihydroperoxide from said organic phase-hydrocarbon mixture, e. washing the crude solid dihydroperoxide with a hydrocarbon stream comprising the same hydrocarbon employed in step b) in a ratio of hydrocarbon to crude solid dihydroperoxide of about 1:1 to about 3:1, f. separating the solid dihydroperoxide from the hydrocarbon wash stream of step 3) and returning said hydrocarbon to the hydrocarbon stream of step b).

* * * * *

UNITED STATES PATENT AND TRADEMARK OFFICE
CERTIFICATE OF CORRECTION

PATENT NO. : 4,053,520
DATED : October 11, 1977
INVENTOR(S) : Glenn E. Miller

It is certified that error appears in the above-identified patent and that said Letters Patent are hereby corrected as shown below:

In Column 10, line 22 delete the number "255 and insert therefor --225--.

In Column 12, line 14 delete the number "3" and insert therefor the letter --e--.

Signed and Sealed this

Eighteenth Day of April 1978

[SEAL]

Attest:

RUTH C. MASON
Attesting Officer

LUTRELLE F. PARKER
Acting Commissioner of Patents and Trademarks